US00PP19583P3

(12) United States Plant Patent
Ackerman et al.

(10) Patent No.: US PP19,583 P3
(45) Date of Patent: Dec. 23, 2008

(54) STRAWBERRY PLANT NAMED 'PS-5298'

(50) Latin Name: *Fragaria ananassa*
Varietal Denomination: PS-5298

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 11/710,528

(22) Filed: Feb. 26, 2007

(65) Prior Publication Data

US 2008/0141404 P1 Jun. 12, 2008

Related U.S. Application Data

(60) Provisional application No. 60/853,002, filed on Oct. 20, 2006.

(51) Int. Cl.
*A01H 5/00* (2006.01)

(52) U.S. Cl. ..... Plt./209

(58) Field of Classification Search ..... Plt./209
See application file for complete search history.

*Primary Examiner*—Annette H Para
*Assistant Examiner*—June Hwu
(74) *Attorney, Agent, or Firm*—Foley & Lardner, LLP

(57) ABSTRACT

This invention relates to a new and distinct variety of strawberry plant named 'PS-5298'. This new strawberry plant named 'PS-5298' is primarily adapted to the growing conditions of the central coast of California, and is primarily characterized by its large plant size; medium to large fruit size; medium to red fruit color; spreading to reflexed calyx segments; medium to strong skin firmness; good fruit production with good flavor, medium green foliage with glossy texture and medium to strong interveinal blistering; and medium to large foliage, concave to flat in shape.

4 Drawing Sheets

Figure 1:
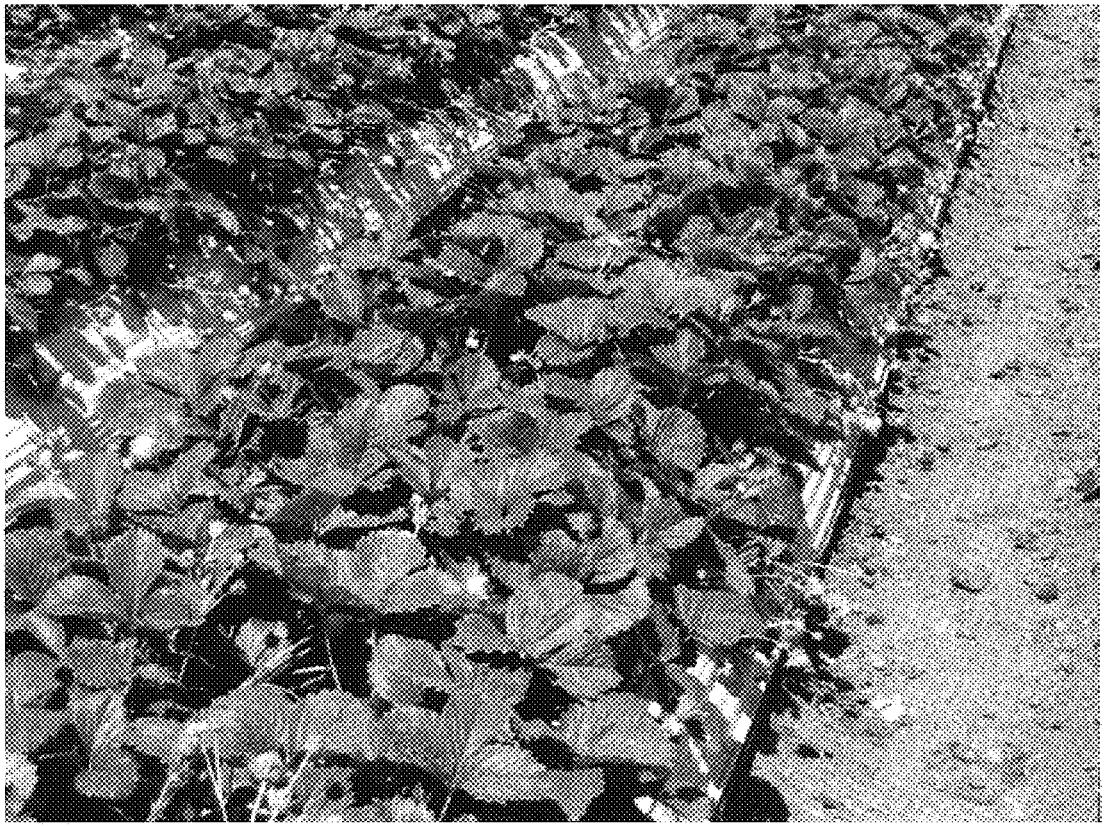

Latin name of the genus and species of the plant claimed: *Fragaria ananassa.*
Variety denomination: 'PS-5298'.

BACKGROUND OF THE INVENTION

The present invention relates to a new and distinct strawberry variety designated as 'PS-5298'. This new variety is a result of a controlled cross made by the inventors, Stephen M. Ackerman, Steven D. Nelson, and Michael D. Nelson, in 1997 between strawberry variety 'PS-592' (patented, U.S. Plant Pat. No. 9,903) and strawberry variety designated 'Aromas' (patented, U.S. Plant Pat. No. 10,451). It is unknown as to which parent variety is the seed parent and which parent variety is the pollen parent. The variety is botanically known as *Fragaria ananassa.*

The seedling resulting from the aforementioned cross was asexually propagated by stolons in a nursery located in Siskiyou County, Calif., and was subsequently selected by the inventors from a controlled breeding plot in Salinas, Calif., in 1999. After its selection, the new variety was further asexually propagated by stolons in both Siskiyou County, Calif. and San Joaquin County, Calif. The new variety was extensively tested over the next several years in fruiting fields of Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-5298' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring and summer production months.

The following traits have been repeatedly observed and are determined to be unique characteristics of 'PS-5298', which in combination distinguish this strawberry plant as a new and distinct variety:

1. Large plant size;
2. Medium to large fruit size;
3. Medium to red fruit color;
4. Spreading to reflexed calyx segments;
5. Medium to strong skin firmness;
6. Good fruit production with good flavor;
7. Medium green foliage with glossy texture and medium to strong interveinal blistering; and
8. Medium to large foliage, concave to flat in shape.

The strawberry varieties that are believed to be most closely related to the new strawberry variety 'PS-5298' are the parental strawberry variety 'PS-592' (patented, U.S. Plant Pat. No. 9,903) and the strawberry variety 'PS-1150' (patented, U.S. Pat. No. 10,780).

In comparison to the similar strawberry varieties 'PS-592' and 'PS-1150', the new strawberry variety 'PS-5298' differs by the following combination of characteristics as described in Table 1:

TABLE 1

| Characteristic | 'PS-5298' | 'PS-592' (U.S. Plant Pat. No. 9,903) | 'PS-1150' (U.S. Plant Pat. No. 10,780) |
|---|---|---|---|
| 1. Color of mature fruit | Red | Red to red orange | Red |
| 2. Average fruit weight (gm) | 23.5 | 23.1 | 17.6 |
| 3. Marketable yield (gm/plt) | 1,362 | 1,392 | 1,010 |
| 4. Attitude of calyx | Spreading to reflexed | Spreading to reflexed | Spreading to collapsing |
| 5. Firmness of skin | Medium to strong | Medium | Strong |
| 6. Time of first harvest | Early | Early | Late |
| 7. Plant size | Large | Large | Medium |
| 8. Foliage color (upper side) | Medium green | Medium green | Medium green |
| 9. Interveinal leaf blistering | Medium to strong | Medium to strong | Weak to medium |
| 10. Foliage glossiness | Medium to strong | Strong | Weak |
| 11. Foliage size | Medium to large | Large | Small |
| 12. Fruiting truss position relative to foliage | Ranges from level with to beneath | Ranges from level with to beneath | Above |

In comparison to the parental strawberry variety 'Aromas', the new strawberry variety 'PS-5298' differs by the following combination of characteristics:

1. 'PS-5298' is partially remontant while 'Aromas' is day-neutral;
2. the shape of the foliage in cross section for 'PS-5298' is slightly concave to flat while 'Aromas' is mostly flat to convex;
3. the insertion of the achenes for 'PS-5298' is level with the surface of the fruit while 'Aromas' is below the surface of the fruit; and
4. the firmness of the fruit flesh for 'PS-5298' ranges from medium to firm while 'Aromas' is very firm.

For identification a series of AFLP molecular markers have been determined for this new variety.

BRIEF DESCRIPTIONS OF THE DRAWINGS

The accompanying color photographs illustrate the overall appearance of typical specimens of the new strawberry variety 'PS-5298', at various stages of development as true as it is reasonably possible with color reproductions of this type. Color in the photographs may differ slightly from the color value cited in the botanical description which accurately describe the color of 'PS-5298'. The depicted plant and plant parts of the new strawberry variety 'PS-5298' were taken in Salinas, Calif., and are approximately 8 to 9 months old.

Figure 2:
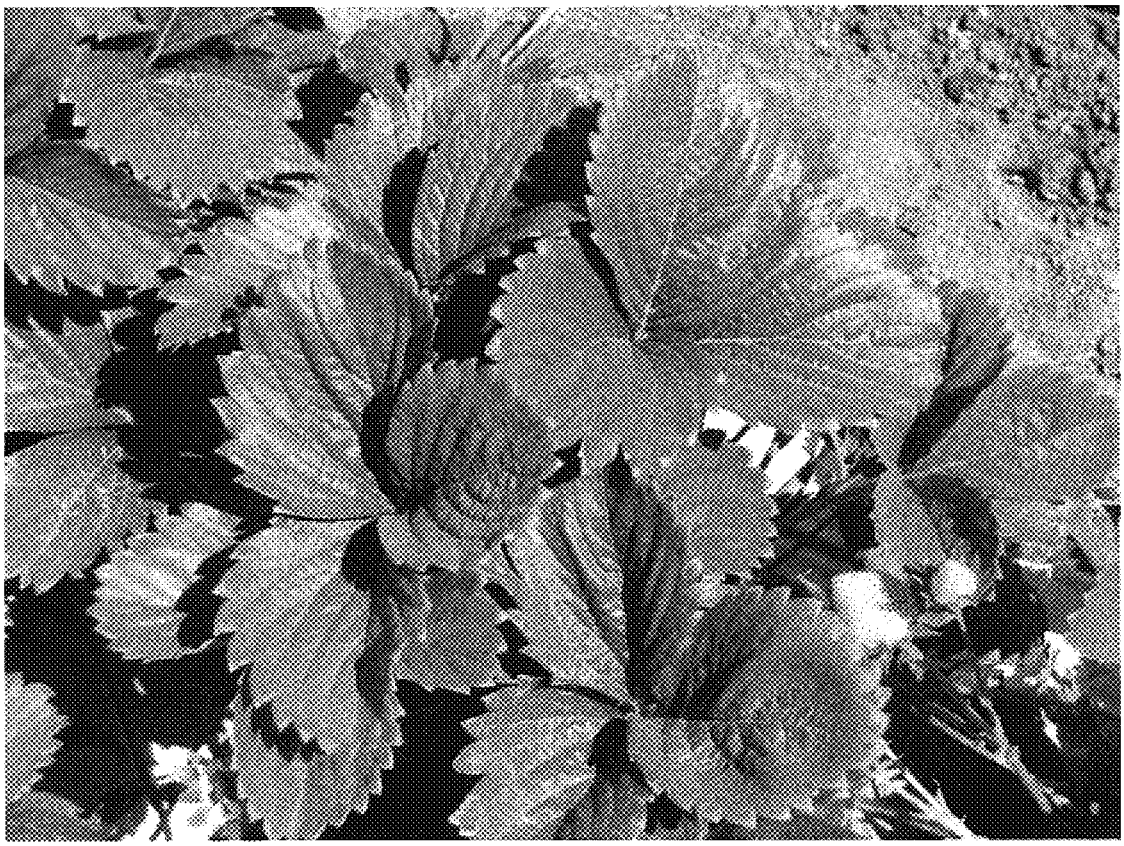
Figure 3:
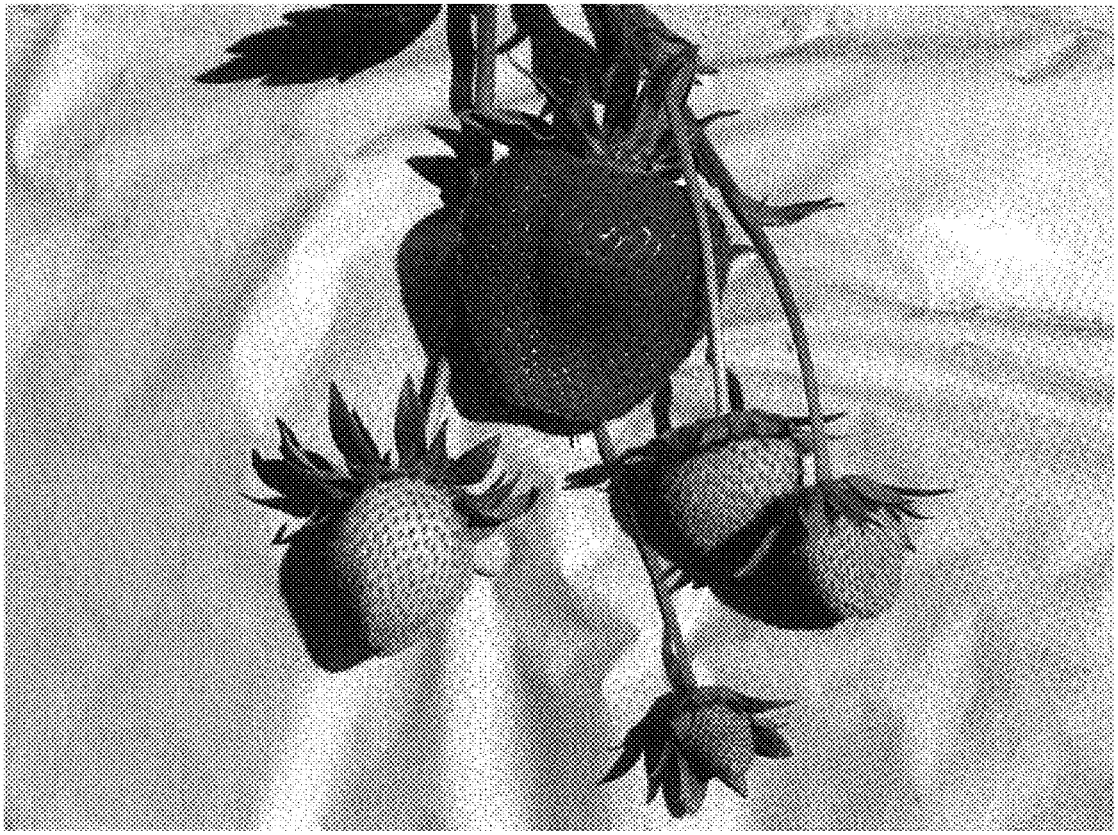
Figure 4:
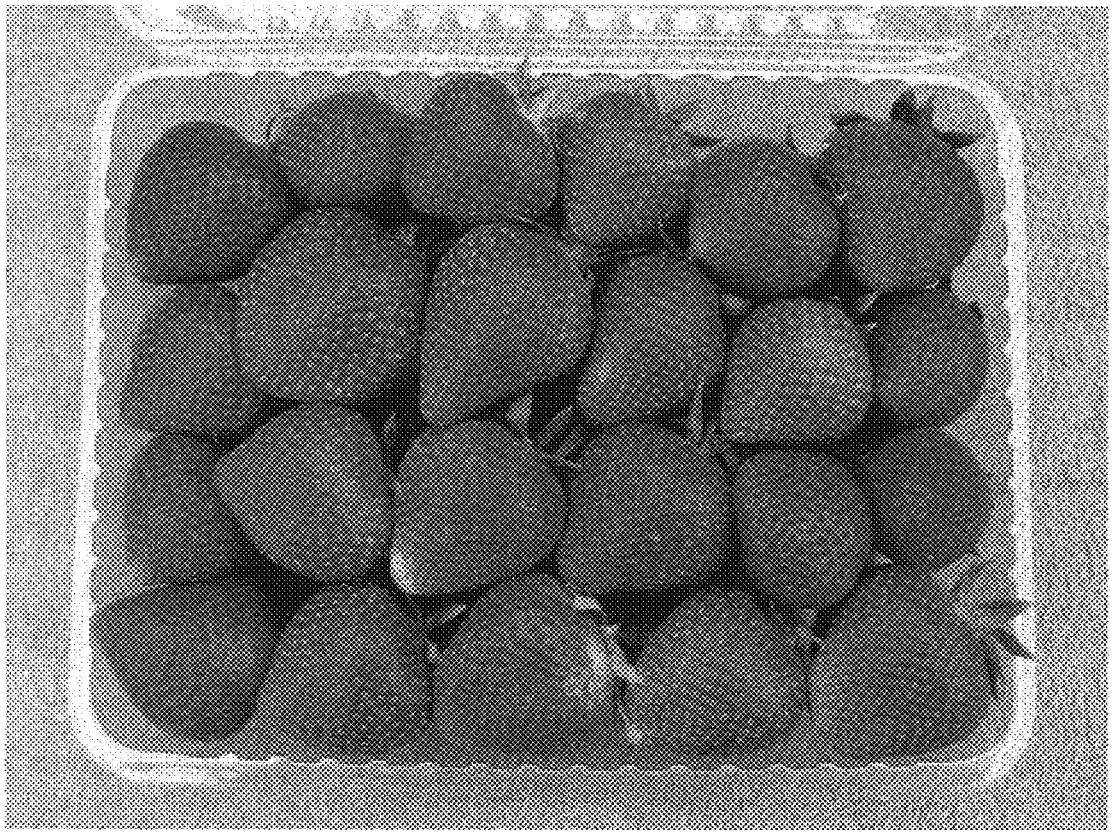

FIG. 1 shows typical fruiting field characteristics taken in the month of June, 2006;

FIG. 2. shows a close-up view of typical leaf structure taken in the month of June, 2006;

FIG. 3 shows typical mature and immature field fruit taken in the month of June, 2006; and FIG. 4 shows a close-up view of fruit taken in the month of July, 2006.

DETAILED BOTANICAL DESCRIPTION

'PS-5298' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new variety 'PS-5298', unless otherwise noted, is based on observations taken during the 2006 growing season in Salinas, Calif. These measurements and ratings were taken from plants of 'PS-5298' dug from a high-elevation nursery located in Siskiyou County, Calif., during the middle of October 2005 and planted approximately 3 weeks later in Salinas, Calif. The approximate age of the observed plants is 7 to 10 months. Yield observations and fruit quality characteristics are averaged from four years of data collected from the 2003 through 2006 growing seasons. Flower measurements and characteristics are from secondary flowers unless otherwise noted. Fruit characteristics and measurements are from secondary fruit unless otherwise noted.

Color terminology where noted follows the Munsell Book of Colors, Munsell Color, Baltimore, Md. (1976).

The following Tables 2–8 describe fruit, plant, stolon, foliage, fruiting truss, flower and pest/disease characteristics of the new strawberry 'PS-5298' in comparison to the similar strawberry varieties 'PS-592' and 'PS-1150'.

TABLE 2

FRUIT CHARACTERISTICS

| Characteristic | 'PS-5298' | 'PS-592' (U.S. Plant Pat. No. 9,903) | 'PS-1150' (U.S. Plant Pat. No. 10,780) |
|---|---|---|---|
| Color of mature fruit | 7.5R 3/10 to 4/10 Red | 7.5R 3/12 to 4/12 Red to orange red | 7.5R 4/10 to 3/8 Red |
| Color of internal flesh | 7.5R 4/10 to 4/12 Medium red | 7.5R 5/10 to 4/10 Light red | 7.5R 4/10 to 4/12 Medium red |
| Length (cm) | 4.9 | 4.8 | 4.2 |
| Width (cm) | 4.3 | 4.3 | 3.7 |
| Ratio length/width | 1.15 Slightly longer than broad | 1.13 Slightly longer than broad | 1.14 Slightly longer than broad |
| Calyx diameter (cm) | 5.0 | 5.0 | 4.2 |
| Average weight (gm) | 23.5 | 23.1 | 17.6 |
| Size | Medium to large | Medium to large | Small |
| Achene color | 5Y 6/8 to 7.5R 3/8 | 5Y 6/8 to 7.5R 3/8 | 5Y 6/8 to 7.5R 3/8 |
| Achenes per berry | 285 | 304 | 293 |
| Achene weight (mg) | 0.64 | 0.61 | 0.56 |
| Marketable yield (gm/plt) | 1,362 | 1,392 | 1,010 |
| Predominant shape | Conical | Conical | Conical |
| Difference in shapes between primary and secondary fruit | Moderate | Moderate | Slight |
| Band without achenes | Absent or very narrow | Absent or very narrow | Absent or very narrow |
| Unevenness of surface | Weak | Weak | Absent or very weak |
| Evenness of color | Slightly uneven to even | Slightly uneven to even | Even |
| Glossiness | Medium to strong | Medium to strong | Strong |

TABLE 2-continued

| FRUIT CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Insertion of achenes | Level with surface | Level with surface | Level with surface |
| Insertion of calyx | Ranges from level with to above fruit | Ranges from level with to above fruit | Ranges from level with to above fruit |
| Attitude of the calyx | Spreading to reflexed | Spreading to reflexed | Spreading to collapsing |
| Size of calyx in relation to fruit diameter | Slightly larger | Slightly larger | Slightly larger |
| Adherence of calyx | Strong | Strong | Strong |
| Firmness of skin | Medium to strong | Medium | Strong |
| Firmness of flesh | Medium to firm | Medium | Medium to firm |
| Distribution of red color of the flesh | Marginal and central | Marginal and central | Marginal and central |
| Hollow center expression | Moderate | Moderate to strong | Moderate to strong |
| Flavor | Good | Very good | Fair |
| Soluble solids (% brix) | 8.0 | 8.0 | 7.4 |
| Time of first flowering | Early | Early | Late |
| Time of first harvesting | Early | Early | Late |
| Harvest period | Late March to early December | Late March to early December | Mid April to early December |
| Type of bearing | Partially remontant | Partially remontant | Partially remontant |

TABLE 3

| PLANT CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Height (cm) | 30.8 | 31.0 | 30.0 |
| Spread (cm) | 36.8 | 35.1 | 28.8 |
| Crowns/plant | 5.3 | 5.0 | 5.0 |
| Size | Large | Large | Medium |
| Habit | Globose | Globose | Globose |
| Density | Medium | Medium to open | Medium |
| Vigor | Strong | Strong | Medium |

TABLE 4

| STOLON CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Average number per plant fruiting field | 1.1 Few to medium | 1.2 Few to medium | 0.8 Few |
| Anthocyanin coloration | 7.5R 5/6 to 6/6 | 7.5R 5/6 to 5/4 | 7.5R 4/6 to 5/6 |
| Anthocyanin intensity | Weak | Medium | Medium to strong |
| Diameter at bract (mm) | 4.7 Thick | 4.4 Thick | 4.2 Medium |
| Pubescence | Medium to strong | Medium | Medium to strong |

TABLE 5

| FOLIAGE CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Foliage: | | | |
| Color of upper surface | 7.5GY 4/4 to 3/4 Medium green | 7.5GY 4/4 Medium green | 7.5GY 4/4 to 3/4 Medium green |
| Color of under side | 5GY 5/4 to 6/4 Light grey green | 5GY 5/4 to 6/4 Light grey green | 5GY 5/4 to 6/4 Light grey green |
| Petiole length (cm) | 23.1 | 21.1 | 19.0 |
| Petiole diameter (mm) | 3.8 | 4.7 | 3.1 |
| Petiolule length (mm) | 14.0 | 15.7 | 9.3 |
| Stipule length (mm) | 20.7 | 20.8 | 14.5 |
| Stipule width (mm) | 8.3 | 8.5 | 8.4 |
| Size bract leaflets | Small | Small to medium | Small |
| Shape in cross section | Slightly concave to flat | Slightly concave | Slightly concave to slightly convex |
| Interveinal blistering | Medium to strong | Medium to strong | Weak to medium |
| Glossiness | Medium to strong | Strong | Weak |
| Number of leaflets | 3 | 3 | 3 to 4 |
| Petiole pubescence | Moderate to sparse | Moderate to sparse | Moderate to sparse |
| Petiole attitude of hairs | Strongly outward | Strongly outward | Strongly outward |
| Stipule anthocyanin coloration | Weak | Medium | Absent or very weak |
| Stipule anthocyanin color | 10RP 4/10 to 4/12 Red purple | 10RP 4/8 to 4/10 Red purple | 10RP 5/6 to 5/8 Red purple |
| Petiole color | 5GY 7/6 to 7/8 Medium yellow green | 5GY 7/6 to 7/8 Medium yellow green | 5GY 7/6 to 7/8 Medium yellow green |
| Petiolule color | 5GY 7/6 to 7/8 Light to medium green | 5GY 7/6 to 7/8 Light to medium green | 5GY 7/6 to 7/8 Light to medium green |
| Stipule color | 5GY 5/6 to 6/6 Light to medium green | 5GY 5/6 to 6/6 Light to medium green | 5GY 7/6 to 7/8 Light to medium green |
| Bracht leaves color | 7.5GY 4/4 to 3/4 Medium green | 7.5GY 4/4 to 3/4 Medium green | 7.5GY 4/4 to 3/4 Medium green |
| Terminal Leaflet: | | | |
| Length (cm) | 9.3 | 9.5 | 7.2 |
| Width (cm) | 7.6 | 8.0 | 6.4 |
| Length/width ratio | 1.22 Much longer than broad | 1.19 Much longer than broad | 1.13 Longer than broad |
| Serrations/leaf | 20.4 | 20.7 | 19.3 |
| Size | Medium to large | Large | Small |
| Shape of base | Acute | Acute | Obtuse |
| Shape of teeth | Obtuse | Obtuse | Obtuse |

TABLE 6

| FRUITING TRUSS CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Length (cm) | 37.4 | 37.3 | 38.1 |
| Position relative to foliage | Ranges from level with to | Ranges from level with to beneath | Above the foliage |

TABLE 6-continued

| FRUITING TRUSS CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| | beneath the foliage | the foliage | |
| Pubescence | Medium | Medium | Medium |
| Anthocyanin intensity | Light | Light | Moderate |
| Anthocyanin color | 10RP 4/10 to 5/10 Red purple | 10RP 4/10 to 5/10 Red purple | 10RP 4/8 to 4/10 Red purple |
| Attitude at first pick | Prostrate | Prostrate | Prostrate |

TABLE 7

| FLOWER CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Petal color | N9.5/90.0%R to N9.25/84.2%R White | N9.5/90.0%R to N9.25/84.2%R White | N9.5/90.0%R to N9.25/84.2%R White |
| Corolla diameter (mm) | 32.3 Large | 30.6 Medium | 30.5 Medium |
| Calyx diameter (mm) | 39.9 | 38.8 | 34.0 |
| Petal length (mm) | 12.4 | 12.1 | 12.5 |
| Petal width (mm) | 12.6 | 11.5 | 10.8 |
| Petal length/width ratio | 0.98 | 1.05 | 1.15 |
| Petals/flower | 5.9 | 6.0 | 6.2 |
| Sepal length (mm) | 16.0 | 15.7 | 13.1 |
| Sepal width (mm) | 6.2 | 6.2 | 5.4 |
| Sepal length/width ratio | 2.57 | 2.54 | 2.42 |
| Sepals/flower | 11.8 | 11.9 | 12.4 |

TABLE 7-continued

| FLOWER CHARACTERISTICS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Sepals color | 5GY 4/6 to 5/6 Medium green | 5GY 4/6 to 5/6 Medium green | 5GY 4/6 to 5/6 Medium green |
| Size of calyx relative to corolla | Larger | Larger | Larger |
| Size of inner calyx relative to outer calyx | Ranges from same size to smaller | Ranges from same size to smaller | Ranges from same size to smaller |
| Relative position of petals | Overlapping | Overlapping | Overlapping |

TABLE 8

| PEST AND DISEASE REACTIONS | | | |
|---|---|---|---|
| Characteristic | 'PS-5298' | 'PS-592' (U.S. Plant Pat. No. 9,903) | 'PS-1150' (U.S. Plant Pat. No. 10,780) |
| Two spotted spider mite | Moderately susceptible | Moderately susceptible | Moderately susceptible |
| Lygus bug | Susceptible | Susceptible | Susceptible |
| Flower thrips | Moderately susceptible | Moderately susceptible | Moderately susceptible |
| Powdery mildew | Moderately susceptible | Moderately susceptible | Moderately susceptible |
| Botrytis fruit rot | Moderately Susceptible | Moderately susceptible | Moderately susceptible |
| Angular leaf spot | Moderately susceptible | Moderately susceptible | Moderately susceptible |
| Virus complex | Unknown | Unknown | Unknown |

We claim:

1. A new and distinct strawberry plant named 'PS-5298', as herein described and illustrated by the characteristics set forth above.

* * * * *